(12) United States Patent
Dimitrova et al.

(10) Patent No.: US 11,170,013 B2
(45) Date of Patent: Nov. 9, 2021

(54) PATHWAY VISUALIZATION FOR CLINICAL DECISION SUPPORT

(71) Applicant: KONINKLIJKE PHILIPS N.V., Eindhoven (NL)

(72) Inventors: Nevenka Dimitrova, Pelham Manor, NY (US); Angel Janevski, New York, NY (US); Nilanjana Banerjee, Armonk, NY (US); Vinay Varadan, New York, NY (US); Sitharthan Kamalakaran, Pelham, NY (US)

(73) Assignee: Koninklijke Philips N.V., Eindhoven (NL)

( * ) Notice: Subject to any disclaimer, the term of this patent is extended or adjusted under 35 U.S.C. 154(b) by 1109 days.

(21) Appl. No.: 14/390,187

(22) PCT Filed: Mar. 27, 2013

(86) PCT No.: PCT/IB2013/052460
§ 371 (c)(1),
(2) Date: Oct. 2, 2014

(87) PCT Pub. No.: WO2013/150420
PCT Pub. Date: Oct. 10, 2013

(65) Prior Publication Data
US 2015/0058322 A1 Feb. 26, 2015

Related U.S. Application Data

(60) Provisional application No. 61/618,892, filed on Apr. 2, 2012.

(51) Int. Cl.
*G06F 16/20* (2019.01)
*G16B 5/20* (2019.01)
(Continued)

(52) U.S. Cl.
CPC ............. *G06F 16/248* (2019.01); *G16B 5/20* (2019.02); *G16B 45/00* (2019.02); *G16B 5/00* (2019.02)

(58) Field of Classification Search
CPC ....... G06F 19/26; G06F 16/248; G16B 45/00; G16B 5/00
See application file for complete search history.

(56) References Cited

U.S. PATENT DOCUMENTS

2003/0218634 A1* 11/2003 Kuchinsky .............. G06F 19/26
715/764
2008/0243394 A1* 10/2008 Petricoin ................. G06F 19/26
702/19

(Continued)

FOREIGN PATENT DOCUMENTS

CN 101989297 A 3/2011

OTHER PUBLICATIONS

Greenblum, S. et al. "The PathOlogist: an automated tool for pathway-centric analysis", BMC Bioinformatics, vol. 12, No. 1, May 4, 2011, p. 133.

(Continued)

*Primary Examiner* — Kristopher Andersen

(57) ABSTRACT

When generating visual representations of gene activity pathways for clinical decision support, a validated pathway database that stores a plurality of validated pathways is accessed, wherein each pathway describes at least one interaction between a plurality of genes. A processor (18) is configured to execute computer-executable instructions stored in a memory (16), the instructions comprising visually representing gene activity level (28) for at least one gene across a plurality of populations, retrieving a pathway (32) from the validated pathway database, wherein the pathway includes the at least one gene, and visually representing gene activity levels for all genes in the pathway. The instructions (Continued)

further comprise a formal visual grammar representation visually representing information flow (36) through interactions between genes in pathway, linking the visual representation of the information flow to actionable information (42) for a clinician, and outputting the visual representation of the information flow and the linked actionable information to the to the clinician.

1 Claim, 9 Drawing Sheets

(51) Int. Cl.
      *G16B 45/00*     (2019.01)
      *G06F 16/248*   (2019.01)
      *G16B 5/00*      (2019.01)

(56) References Cited

U.S. PATENT DOCUMENTS

2009/0299646 A1   12/2009   Shams et al.
2011/0077964 A1    3/2011   Janevski et al.

OTHER PUBLICATIONS

Vaske, C. et al. "Inference of patient-specific pathway activities from multi-dimensional cancer genomics data using Paradigm", Bioinformatics, vol. 26, No. 12, Jun. 15, 2010, pp. 1237-1245.

Gehlenborg, et al., "Visualization of omics data for systems biology", Nature Methods Supplement, vol. 7, No. 3, Mar. 2010, pp. 56-68.

\* cited by examiner

PATHWAY VISUALIZATION FOR CLINICAL DECISION SUPPORT

CROSS-REFERENCE TO PRIOR APPLICATIONS

This application is the U.S. National Phase application under 35 U.S.C. § 371 of International Application No. PCT/IB2013/052460, filed on Mar. 27, 2013, which claims the benefit of U.S. Provisional Application No. 61/618,892, filed on Apr. 2, 2012. This application is hereby incorporated by reference herein.

The present application finds particular application in clinical decision support systems. However, it will be appreciated that the described technique may also find application in other diagnostic systems, other medical scenarios, or other clinical techniques.

Diagnostic and therapy decisions in oncology are largely based on the underlying biology. Understanding the mechanisms of the disease plays a key role in cancer research, but can also help clinicians in making decisions and tracking the progress of the disease.

Currently, next generation sequencing is close to a revolution to provide information that was not previously accessible to the clinicians for diagnosis and prognosis of a particular disease. Both the depth and the resolution of this information create an enormous amount of data. Molecular signatures that have previously been studied typically do not explicitly capture the underlying cellular mechanisms (pathways) and are therefore limited in their ability to explain the real root cause and the ability to create an understanding of how to treat the patient within the realm of available therapy choices. Biological pathways are an intuitive way of presenting this information. Existing methods have focused on computing how to rank pathways and their deregulation in the context of a particular clinical question.

In current practice, patients diagnosed with cancer are stratified based on clinicopathological data into groups that determine prognosis (e.g. in terms of time to cancer progression or recurrence), response to or selection of therapy, etc., but the basis for stratification is typically presented as a table or a list of markers and clinical data. Also, classification of patients based on high throughput molecular data through the statistical selection of a set of features that jointly differentiate between clinically relevant classes of patients results in just a single score or a list of genes levels. Moreover, these methods do not explicitly capture how elements of genetic regulation may impact the underlying condition that the doctor is trying to assess beyond a fairly simple rule-based association, which is already present in the clinical guidelines. However, for patients that are clearly not falling within these boundaries of a clinical guideline there is very little information that can be elicited from the massive amounts of data generated by next generation sequencing.

The present application relates to new and improved systems and methods that facilitate visually representing gene activity levels, pathways and interactions in order to provide therapy recommendations to a clinician, which overcome the above-referenced problems and others.

In accordance with one aspect, a system that facilitates visualizing gene activity pathways using a visual grammar that defines visual elements associated with gene expression, gene activity level, and information flow, for clinical decision support includes a validated pathway database that stores a plurality of validated pathways, each of which describes at least one interaction between a plurality of genes, and a processor configured to execute computer-executable instructions stored in a memory. The instructions comprise visually representing gene activity level for at least one gene across a plurality of populations, retrieving a pathway from the validated pathway database, wherein the pathway includes the at least one gene, and visually representing gene activity levels for all genes in the pathway. The instructions further comprise visually representing information flow through interactions between genes in pathway, linking the visual representation of the information flow to actionable information for a clinician, and outputting the visual representation of the information flow and the linked actionable information to the clinician.

In accordance with another aspect, a non-transitory computer-readable storage medium has stored thereon computer-readable instructions for visualizing gene activity pathways using a visual grammar (230) that defines visual elements associated with gene expression using a visual grammar that defines visual elements associated with gene expression, gene activity level, and information flow, for clinical decision support, the instructions comprising visually representing gene activity level for at least one gene across a plurality of populations, retrieving a pathway from a validated pathway database, wherein the pathway includes the at least one gene, and visually representing gene activity levels for all genes in the pathway. The storage medium further comprises instructions for visually representing information flow through interactions between genes in pathway, linking the visual representation of the information flow to actionable information for a clinician, and outputting the visual representation of the information flow and the linked actionable information to the clinician.

According to another aspect, a method of visualizing gene activity pathways for clinical decision support using a visual grammar (230) that defines visual elements associated with gene expression, gene activity level, and information flow comprises visually representing gene activity level for at least one gene across a plurality of populations, retrieving a pathway from a validated pathway database, wherein the pathway includes the at least one gene, and visually representing gene activity levels for all genes in the pathway. The method further comprises visually representing information flow through interactions between genes in pathway, linking the visual representation of the information flow to actionable information for a clinician, and outputting the visual representation of the information flow and the linked actionable information including at least one therapy plan to the clinician.

Still further advantages of the subject innovation will be appreciated by those of ordinary skill in the art upon reading and understanding the following detailed description.

The innovation may take form in various components and arrangements of components, and in various steps and arrangements of steps. The drawings are only for purposes of illustrating various aspects and are not to be construed as limiting the invention.

The subject innovation overcomes the aforementioned problems by addressing a clinical need for improved diagnostics with visualization tools for high-throughput molecular profiling data in general, and DNA sequencing data in particular. The described systems and methods aid in visualizing of the statistical analysis results in the context of pathway evaluation to stratify cancer patients with high sensitivity and specificity, which results in better patient outcomes, more targeted treatment, and substantial savings in medical cost.

There is an overwhelming amount of molecular information becoming available that can be used for diagnostic and therapy planning purposes. The modalities span DNA sequencing, transcriptome sequencing, methylation sequencing, etc. Providing clear and intuitive view of this information and ability to interact with this information is technically challenging. The described systems and methods facilitate visualizing this information in a specific biological pathway using high throughput molecular profiling data derived from human samples in order to support prognosis and therapy selection in cancer and other diseases. Known biological knowledge about gene function and gene interactions is captured as biological pathways, on which are overlaid the activity levels of genes as measured from multiple molecular modalities, such as copy number and gene expression data. Visualization of various parameters is facilitated, including but not limited to: individual genes within a single patient; pathway information in a population of patients; pathway information across different clinical studies or across patients from different hospitals or across different regiments of pathway activity levels in patients and these pathway activity levels can then be used to differentiate one patient from another; pathway information representing response to a particular therapy regimen; etc. In another embodiment, additional clinical data associated with the patient is provided and accompanies the gene activity and pathway information. For example, if metabolic pathways are being visualized, then it may be pertinent to include clinical information indicating that the patient is diabetic.

The described systems and methods can be used in conjunction with a pathway evaluation model such as a pathway information flow model. In this manner the clinician is provided with a technique to interpret whole genome molecular profiling data acquired from this patient, to choose a much more tailored therapy for the patient. In effect, massive and complex amounts of data are converted into reduced visual representations that are more intuitively interpretable by the clinician, to guide the clinician's choices thereby significantly improving patient response while reducing the overall costs and toxicities for the patient.

Figure 1:
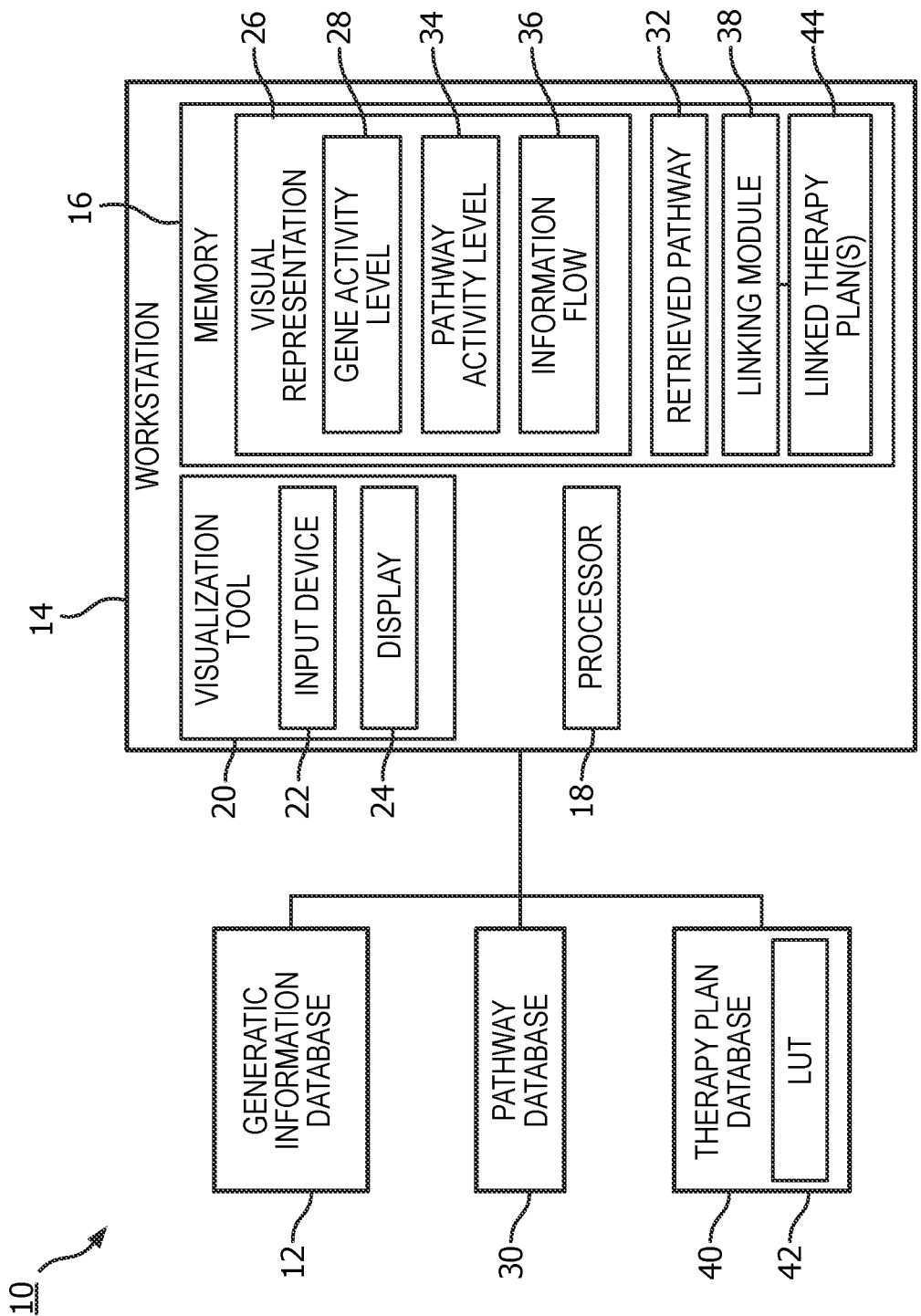
FIG. 1 illustrates a system that facilitates providing a clinician with a visual representation of a gene activity pathway for clinical decision support.

FIG. 1 illustrates a system 10 that facilitates providing a clinician with a visual representation of a gene activity pathway for clinical decision support. The system 10 includes a genetic information database 12 that includes gene activity data for a plurality of patients including a current patient, as well as gene activity data for one or more normal patient populations and one or more tumor patient populations. A workstation 14 (e.g., a computer or the like), includes a memory 16 (i.e., a computer-readable storage medium) that stores computer-executable instructions, and a processor 18 that executes the computer-executable instructions to perform various methods, techniques, functions, and the like as described herein. In one embodiment, the memory is distributed and/or provided as a service, such as a cloud-based storage service wherein pathways and/or associated information are stored in the cloud. The system further comprises a visualization tool 20 including an input device 22 (e.g., a keyboard, mouse, stylus, microphone, touchscreen, touchpad, or the like) via which a user or clinician inputs information into the workstation, and a display on which information (e.g., visualizations or mappings, therapy recommendations, etc.) is presented to the user. In one embodiment, the visualization tool and/or input device are installed or otherwise provided as an app on a smartphone, tablet, or other personal computing device.

The memory stores a visual representation module 26 that, when executed by the processor, generates visual representations that are intuitively interpretable by the clinician. For instance, the visual representation module generates a gene activity level mapping 28 that shows a current patient's gene activity level relative to an average activity level for the gene in a tumor population and an average activity level for the gene in a normal population. Once gene activity level has been visualized, the processor retrieves a validated pathway for the gene is retrieved from a validated pathway database 30, and the retrieved pathway is stored in the memory 16. The visual representation module 26 generates a pathway activity level mapping 36 that shows activity levels of all genes in the retrieved pathway, and an information flow diagram 36 that shows relationships between the genes in the pathway. Once the information flow diagram is generated, a linking module 38 is executed by the processor to identify one or more therapy plans in a therapy plan database 40 that can be used to treat the patient based on the information contained in the mappings 28, 34 and the information flow diagram 36. In one embodiment, therapy plans in the therapy plan database are tagged (e.g., using metadata) as corresponding to one or more particular pathways and/or information flows. In another embodiment, the therapy plan database 40 and/or the memory 16 includes a therapy plan lookup table (LUT) that correlates therapy plans to mappings and/or information flows. One or more identified linked therapy plans is stored in the memory 16. The processor 18 outputs the gene activity level mapping 28, the pathway activity level mapping 34, the information flow 36, and the linked therapy plan(s) to the clinician via the display 24.

As stated above, the system 10 includes the processor 18 that executes, and the memory 16 that stores, computer-executable instructions (e.g., routines, programs, algorithms, software code, etc.) for performing the various functions, methods, procedures, etc., described herein. Additionally, "module," as used herein, denotes a set of computer-executable instructions, software code, program, routine, or other computer-executable means for performing the described function, or the like, as will be understood by those of skill in the art.

The memory may be a computer-readable medium on which a control program is stored, such as a disk, hard drive, or the like. Common forms of non-transitory computer-readable media include, for example, floppy disks, flexible disks, hard disks, magnetic tape, or any other magnetic storage medium, CD-ROM, DVD, or any other optical medium, RAM, ROM, PROM, EPROM, FLASH-EPROM, variants thereof, other memory chip or cartridge, or any other tangible medium from which the processor can read and execute. In this context, the systems described herein may be implemented on or as one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, Graphical card CPU (GPU), or PAL, or the like.

The described systems and methods facilitate clinical decision support visualization that uses known biological pathways and/or inferred regulatory networks to highlight pathway (network) activity in the context of understanding the clinical condition of a patient and/or in the context of contrasting different patient groups. These techniques employed multiple high throughput molecular modalities such as gene expression and copy number data measured on the same patient sample.

The clinical decision support aspect of these techniques involves the use of multi-modality molecular profiling data on a single patient along with pathway database resources (for example, National Cancer Institute Pathway Interaction Database) and a pathway visualization engine. In this manner, an intuitive and accurate visual representation of gene activity is generated in a consistent manner that is supported on the technical side with a "visual grammar" that can express the deviation from normal activity of a gene in the context of a biological network (or a pathway). Thus a new diagnostic device is provided that is supported by a software and/or a hardware implementation (for robustness and speed in a clinical setting).

Figure 2:
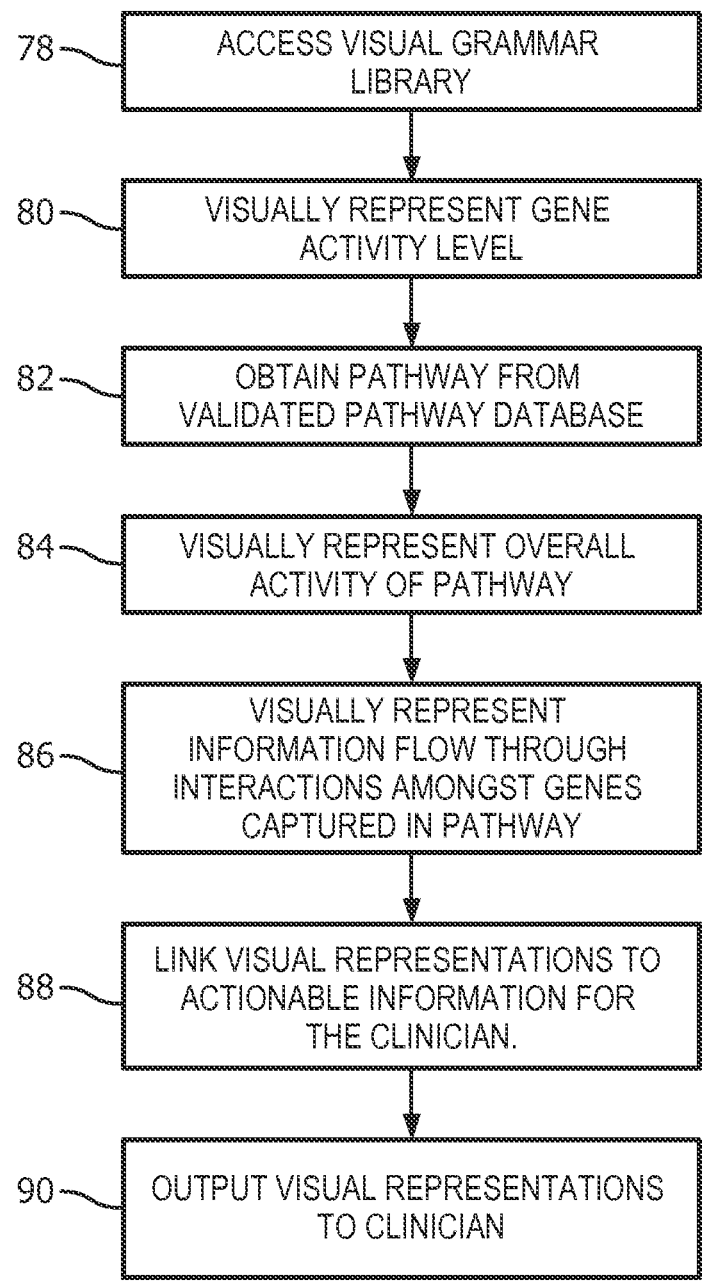
FIG. 2 illustrates a method of visually or graphically representing to a user or clinician a single clinical value (e.g., gene activity or the like) to a three-dimensional (3D) space.

FIG. 2 illustrates a method of visually or graphically representing to a user or clinician a single clinical value (e.g., gene activity or the like) to a three-dimensional (3D) space. The 3D space may be a color space (e.g., RGB, CMY, or the like), a 3D space that is presented to the user as a textured or patterned 3D graph or representation, or any other suitable 3D space. The method can be applied to both biological pathways and biological networks and implements a visual grammar that can translate activity of each gene and pathway into a visual representation. The visual representation can use color, texture, shape, and/or temporal aspects (e.g., flashing or motion). In one embodiment, the function of a gene and/or the genomic locus (e.g. transcription factor that regulates the activity of many genes or a non-coding RNA that can keep the level of gene expression at a certain level or disrupt activity of many genes) is visually represented such that the frequency of the flashing or motion is proportional to the gene activity level. Additionally, the method facilitates modularization in that a smaller part of a network can become a single node at the level of interacting pathways. The method also facilitates guiding choices in clinical decision support by performing visualization of pathways that are functionally relevant from a clinician's point of view, for instance: per subtype of cancer, which are most likely pathways that are varying within a particular subtype; and/or by highlighting pathways that are potentially interesting for a specific set of regimens (e.g., clinical decision choices) relevant from the clinical guideline point of view. The suggested visualizations are supported by sufficient clinical evidence. For example, if one of the drugs in the regimen has anti-angiogenesis action, it is clinically relevant to visualize pathways that are related to vascular development.

Accordingly, the method comprises accessing a visual grammar library or the like, at 78. The method further comprises visually representing a gene activity (or some other parameter) level (e.g., on a graphical display or printed sheet) to a user via a user-selected visual grammar, at 80. At 82, a relevant pathway is obtained from a database of validated pathways. At 84, overall pathway activity is represented visually. At 86, information flow through the interactions amongst genes captured in the pathway is represented. At 88, the foregoing visual representations are linked to actionable information for a clinician. At 90, the visual representations are presented to the clinician for analysis. The foregoing acts are described in greater detail with regard to FIGS. 3A-9.

Figure 3A:
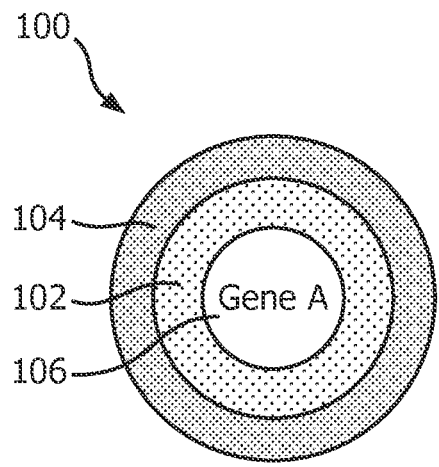
FIGS. 3A-3D illustrate examples of a visual grammar in which each node in a pathway is represented by a visual element using color, texture, shape, etc., to represent high-throughput molecular profiling data from single patient or a subset of patients in the context of specific biological node (e.g., gene, locus, etc.).
Figure 3B:
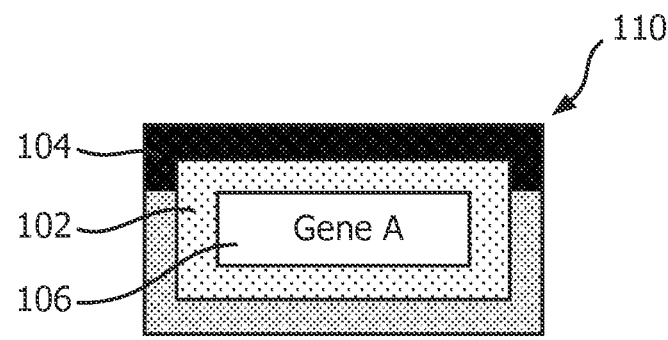

FIGS. 3A-3D illustrate examples of a visual grammar in which each node in a pathway is represented by a visual element using color, texture, shape, etc., to represent high-throughput molecular profiling data from single patient (or a subset of patients in the context of specific biological node (e.g., gene, locus, etc.). The visual element may be, for example a color-coded or texture-coded circle, rectangle (or any desired shape), a temperature map, pie chart, bar plot, mathematical function (e.g. survival curve), or the like. In FIG. 3A, a representation 100 is provided of the overall mean gene expression value of a tumor population 102 and a normal population 104. In the middle is shown the value of gene expression value of a current patient 106. In FIG. 3B the same gene expression values 102, 104, 106 are represented using a color-coded rectangular node 110. Each of the visual elements in FIGS. 3A, 3B, 3C, 3D is a visual element representing a gene, its expression status for a patient, and at least one other patient population (e.g., normal and tumor, or two subtypes (e.g. luminal and basal subtypes in breast cancer, note that 3D is representing only one patient within a single patient population).

Figure 3C:
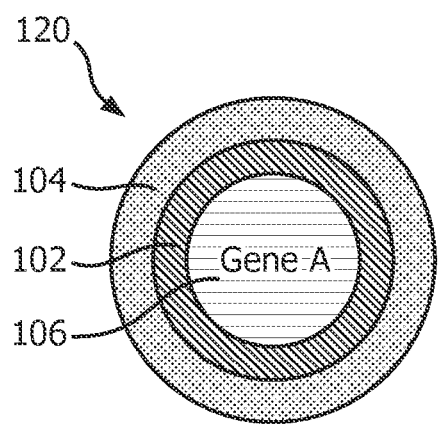
Figure 3D:
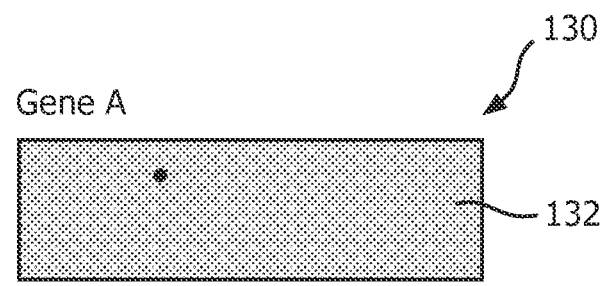

In FIG. 3C a representation 120 of the gene expression values 102, 104, 106 is illustrated with different textures or patterns representing the normal population, tumor population, and the patient, respectively. FIG. 3D shows a representation 130 that employs a temperature map 132 that visually expresses the range of values and where the expression value of the current patient falls within the range of values.

In one embodiment, the overall tumor and normal populations includes all such patients within a hospital network or the like, and the current patient may be a single patient or a subset of patients exhibiting particular clinical variables. Additional concentric circles (or rectangles, etc.) can be added to represent multiple layers of patient stratification (e.g. responders and non-responders within the tumor group) to a particular drug. In another embodiment, a color level is associated with intensity of expression for a positive outcome vs. poor outcome.

Figure 4:
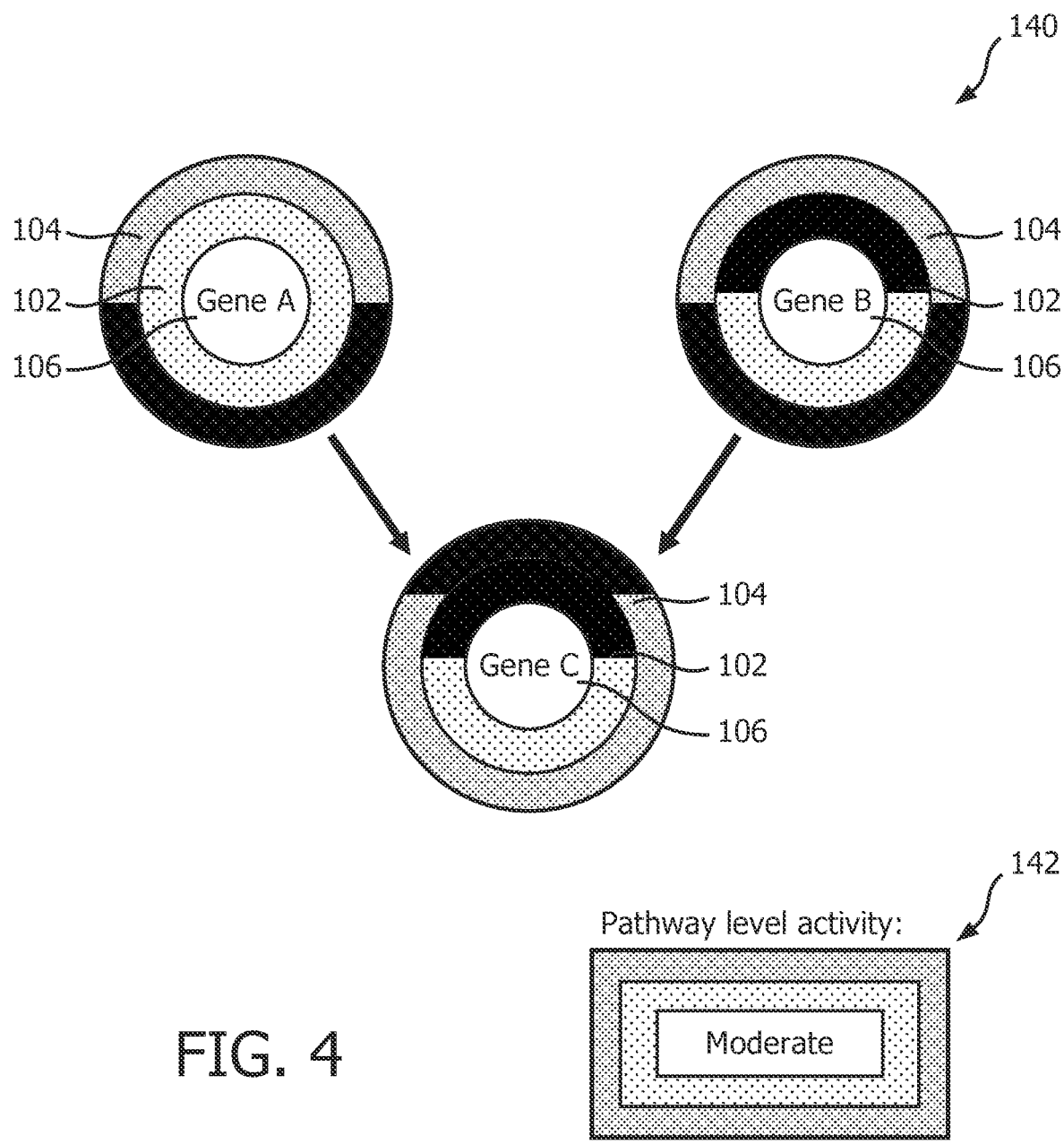
FIG. 4 illustrates a mapping of gene activity.
Figure 9:
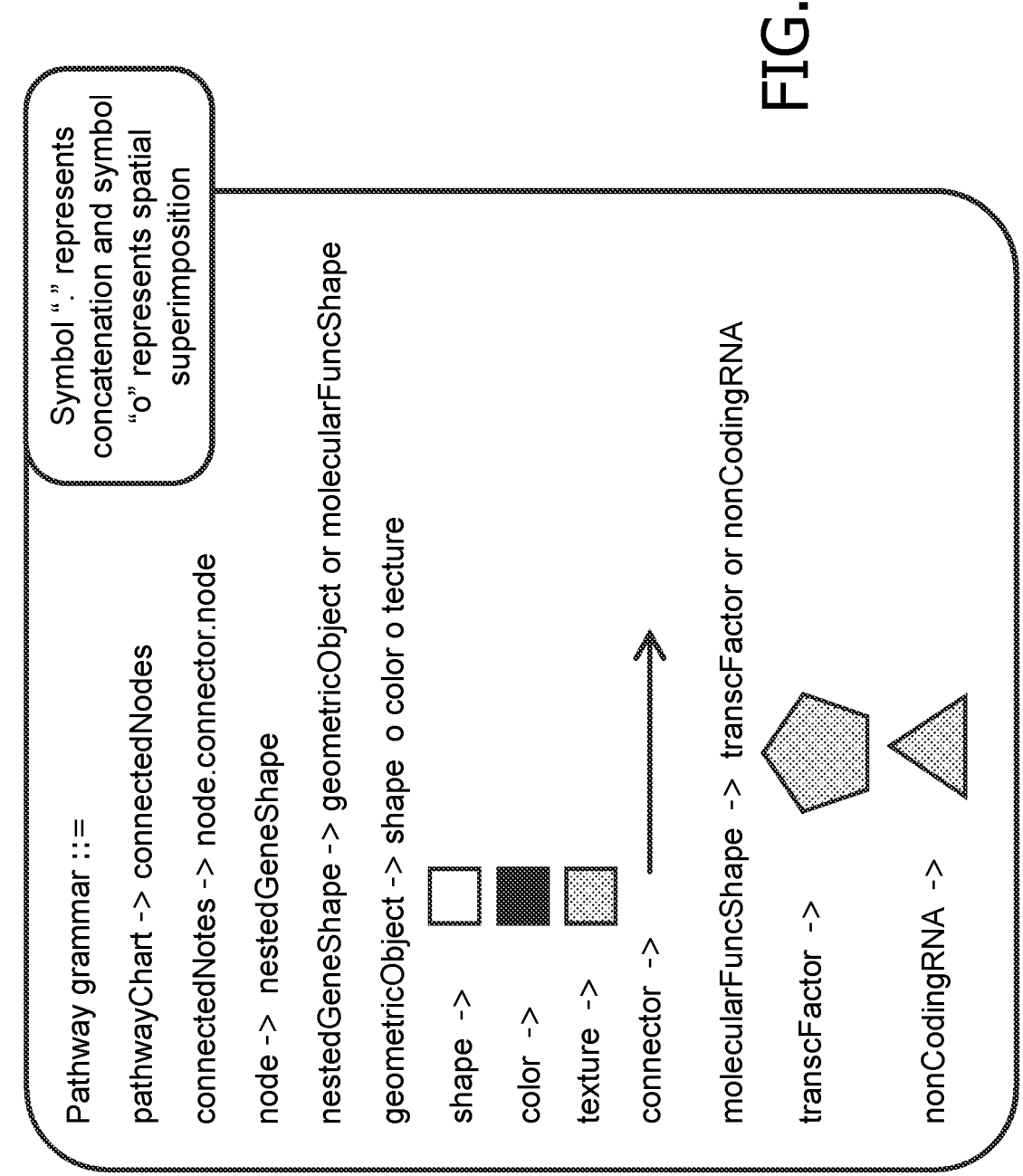
FIG. 9 illustrates an example of a pathway visual grammar.

FIG. 4 illustrates a mapping (e.g., a visual representation) 140 of gene activity, such as is generated at 80 (FIG. 2) and as shown in FIG. 9. The mapping is a visualization of color-based, high-throughput molecular profiling data from single patient in the context of specific biological pathway relative to a population. The mapping is generated from a set of existing expression values from one or more of: SNP data (e.g. number of mutations within a gene), copy number polymorphisms (number of copies), gene expression level, protein expression level, DNA methylation level of a genetic locus, histone methylation level of a genetic locus, histone acetylation level of a genetic locus, phosphorylation signal (on or off) of a particular protein, etc. The first step is to visually represent the level of activity of each gene: using multiple molecular modalities such as gene expression data and copy number variation data, a probability is determined that a particular gene is over-expressed, under-expressed or is at baseline levels compared to normal tissue. For this step, inferring the level of a gene can be performed using predetermined thresholds with respect to the mean of the distribution (one could also use a simple statistical test) and the gene can be represented via one of the several options.

Under a rule-based approach, maps a range of values from the under-expressed to one or more of: a single color (e.g., blue) and another range of values from the over-expressed to another color (e.g., red); a single texture; a combination of color and texture; and a temporal element that slightly changes the color over time (e.g., pulsates) or the shape used to represent the carious population values (e.g., in cases where the gene is highly variable).

In another approach, visual color is represented in the hue-saturation-brightness (HSB) space corresponding to an intensity (level) of gene expression, which is generated by a continuous function mapping. In one embodiment, if a gene has a range of values: $r=[a,b]$ then values are assigned in the HSB space. For each point $r_i \in [a,b]$ a linear function is chosen to map the value in $h_i=f(r_i)$; however, this function can also be a quadratic or logarithmic function depending on the dynamic range of values. In another embodiment, when there are functional designations of the genes such as, e.g., tumor suppressors and oncogenes, a different slice of the HSB space is assigned to these different functional categories. For instance, hue is mapped to values from, e.g., 0 to 60 for oncogenes and mapped to values from, e.g., 120 to 180 for tumor suppressors.

FIG. 4 shows an instance of a possible visualization of the same pathway where for each gene there are multiple circles representing a given node with respect to the mean intensity values of the tumor population 102, mean intensity values of the normal population 104, and the intensity values for a patient 106 (e.g., John Doe), respectively. The overall pathway level 142 is represented with a different visual element (in this case a rectangle).

Figure 5:
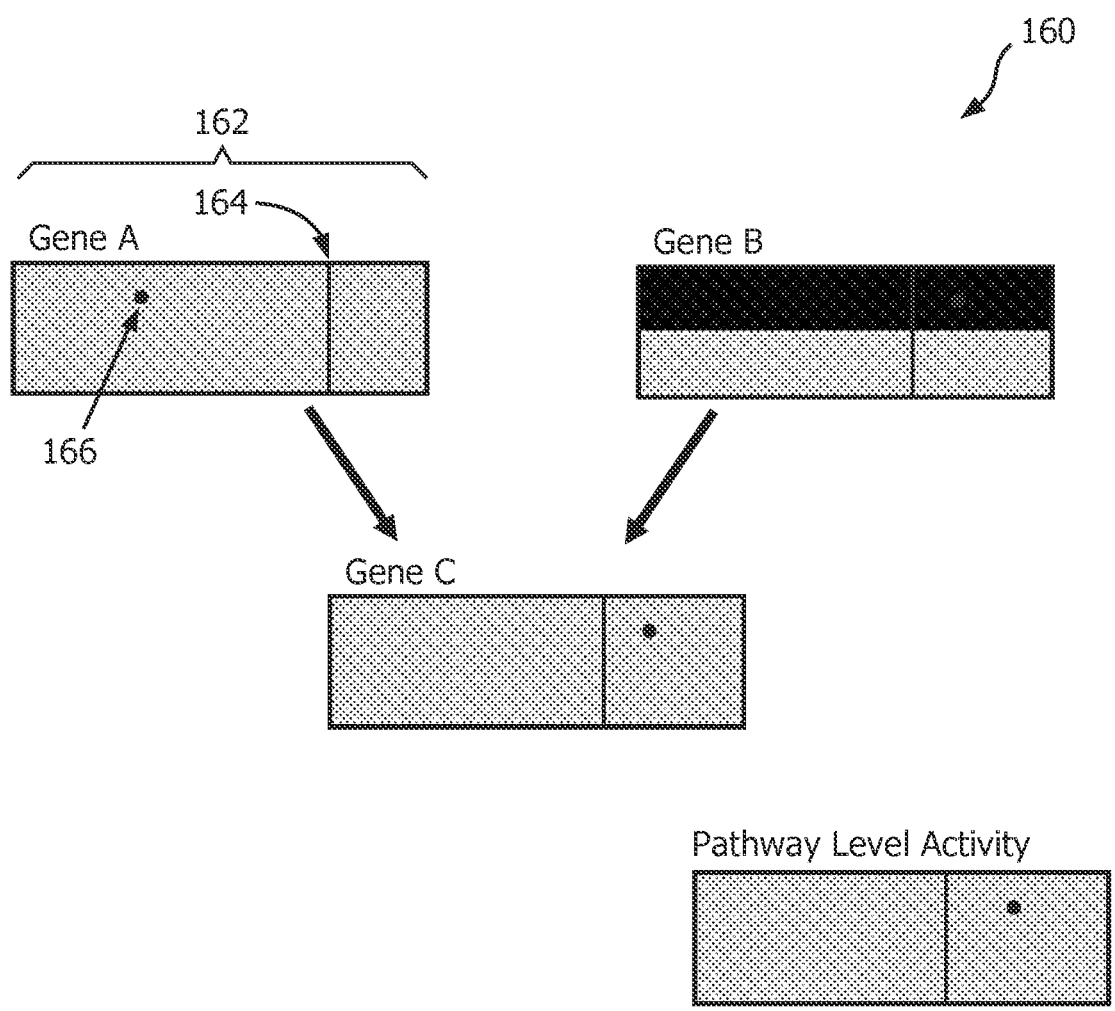
FIG. 5 illustrates a mapping represented with a temperature graph.

FIG. 5 illustrates a mapping 160 represented with a temperature graph that shows an overall range of values 162, a vertical line that corresponds to the tumor population mean intensity value 164 (e.g., for a tumor population or for a normal population), and a dot representing the current patient's intensity value(s) 166. The mapping is a visualization of color-based, high-throughput molecular profiling data from single patient in the context of specific biological pathway relative to continuum of a population. This representation can be used for each gene in the pathway and for the overall activity of the pathway. It should be noted that the overall activity of the pathway may reflect the p-value that is derived from the overall activity assessment (e.g., with a hypergeometric test) or derived from the information flow.

Figure 6:
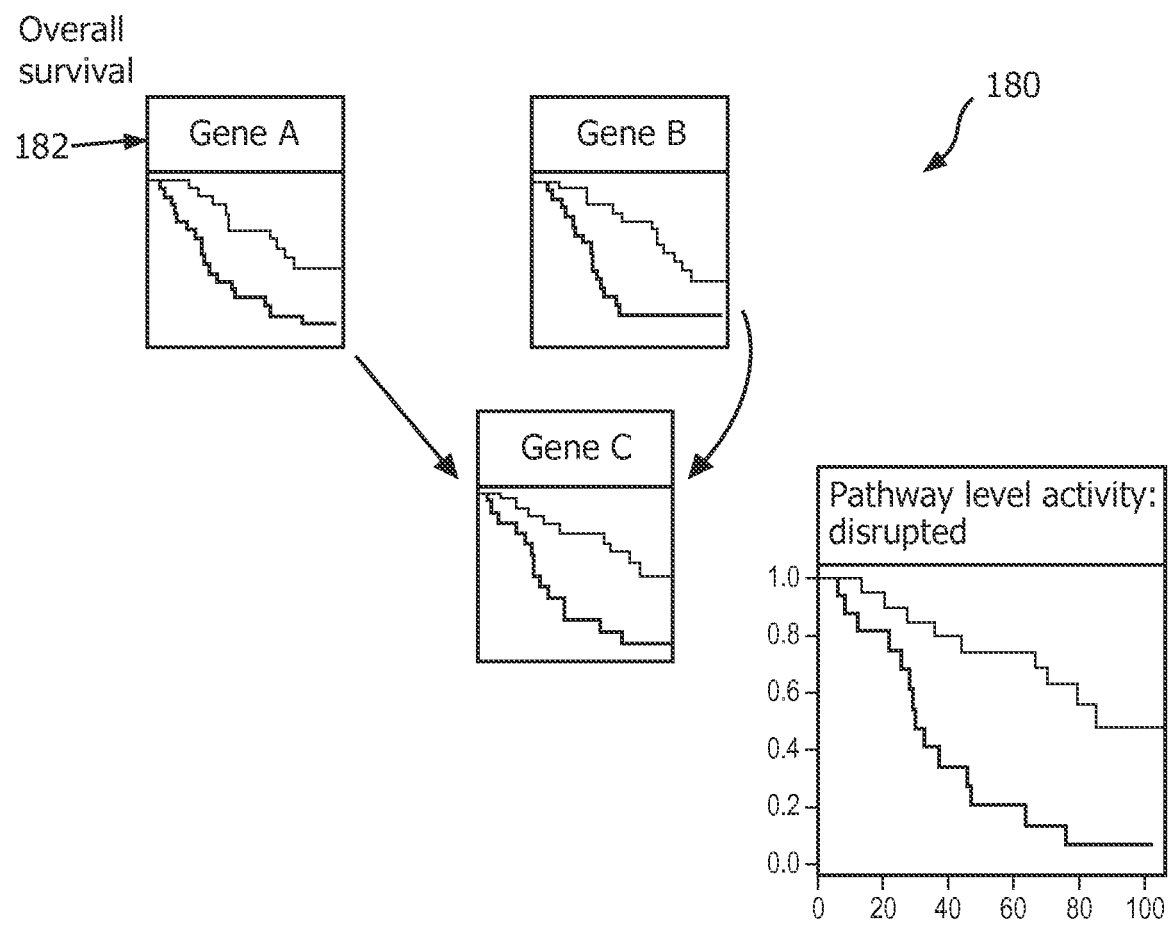
FIG. 6 illustrates a visualization of multiple genes within a pathway and association of a gene with good or poor outcome.

FIG. 6 illustrates a visualization 180 of multiple genes within a pathway and association of a gene with good or poor outcome. The visualization shows color-based, high-throughput molecular profiling data from single patient 182 in the context of specific biological pathway with regard to survival of patient groups. Each gene may individually be associated with good or poor outcome. However, the overall synergistic effect within a pathway could be more strongly associated with a particular outcome, and so the overall activity of a pathway (normal vs. disrupted) is visualized with respect to outcome.

FIGS. 4-6 thus illustrate mappings or visualizations of overall activity of a given pathway, as is performed at 84 (FIG. 2) once the pathway is obtained from the validated pathway database (at 82). In one embodiment, rule-based visualization is performed whereby a range of values is mapped from the inactive genes, moderately active genes, and hyperactive genes, compared to normal tissue. In one example, a single color (e.g., blue) is used for the inactive genes, and another color is used for over-expressed genes (e.g., red). In another example, a single texture is used for each of the inactive genes, moderately active genes, and hyperactive genes. In another example a combination of color and texture is used to represent different gene activity levels. If the pathway level is highly variable, a temporal element can be employed that slightly changes the color over time (e.g., pulsates) or the oval (or other shape) used to represent the patient, tumor, and normal populations respectively.

In another embodiment, the mapping is generated using visual color in the HSB space corresponding to respective intensities of pathway activity levels, and is generated by a continuous function. For instance, the input to this continuous function can be the p-value after a hypergemetric test is applied. The input can also correspond to the information flow level. For example, if a pathway activity has a range of values such that: $r=[a,b]$, then values are assigned in the HSB space (i.e., hue-saturation-brightness). For each point $r_i \in [a,b]$, a function is selected to map the value in $h_i=f(r_i)$. It will be appreciated that the function need not be linear function, but can also be a quadratic or logarithmic function depending on the dynamic range of values.

Additionally or alternatively, if there are functional designations of the pathways (e.g., signaling cascade vs. transcription activation), there is a different slice of the HSB space assigned to these different functional categories. For instance, hue is mapped to values from, e.g., 0 to 60 for transcription activation, and mapped to values from, e.g., 120 to 180 for signaling, where hue is the angle around the central vertical axis in the HSV cylindrical space. Brightness corresponds to the intensity of the signal.

Figure 7A:
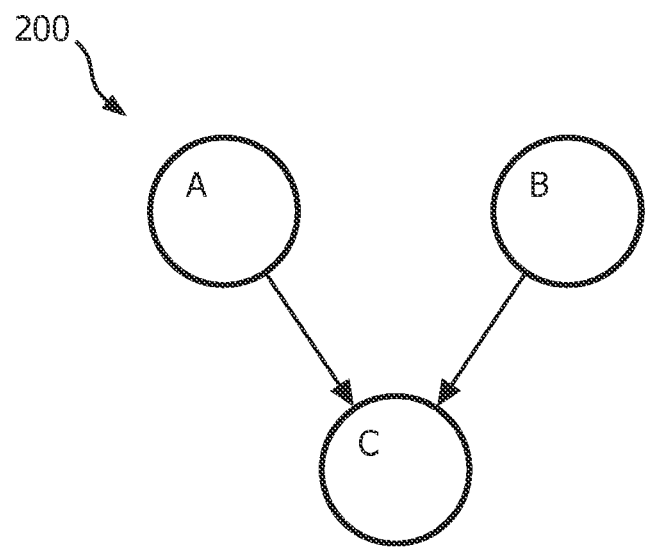
FIGS. 7A and 7B illustrate visual representations of an information flow through the interactions amongst genes captured in the pathway.
Figure 7B:
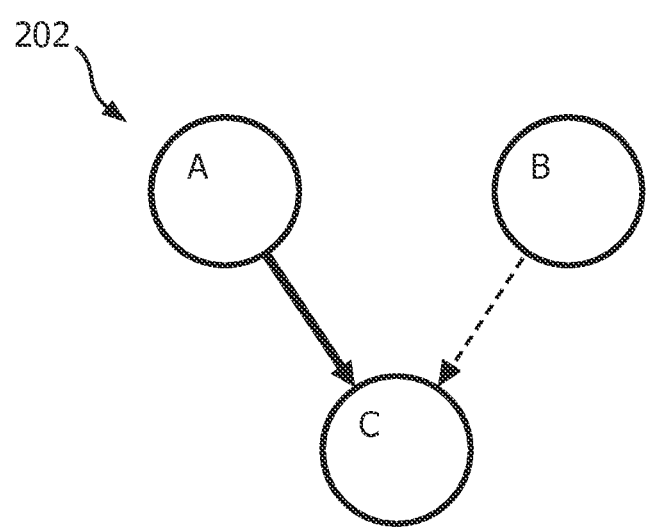

FIGS. 7A and 7B illustrate visual representations 200, 202, respectively, of an information flow through the interactions amongst genes captured in the pathway, as is performed at 86 (FIG. 2). For example, a pathway is assumed that defines an interaction between GeneA, GeneB and GeneC as shown in FIG. 7A. The interaction in the pathway says that either GeneA or GeneB is over-expressed in order for GeneC to be over-expressed. Using the probabilities of over-expression, repression, and baseline expression for GeneA, GeneB, and GeneC in the patient, a determination is made regarding whether this particular interaction was activated. In other words, the probability of this interaction ($I_1$) is the probability of GeneB or GeneA being over-expressed. A different color is assigned for the arc between GeneA and GeneB based on the probability of this link being active. If there is a high probability that gene C is active and geneA is active then a strong first color is assigned to the interaction there between (green in the example of FIG. 7B). If the geneC is active but geneB is inactive, then we assign a strong second color (e.g., red) to the interaction between genes B and C.

Figure 8:
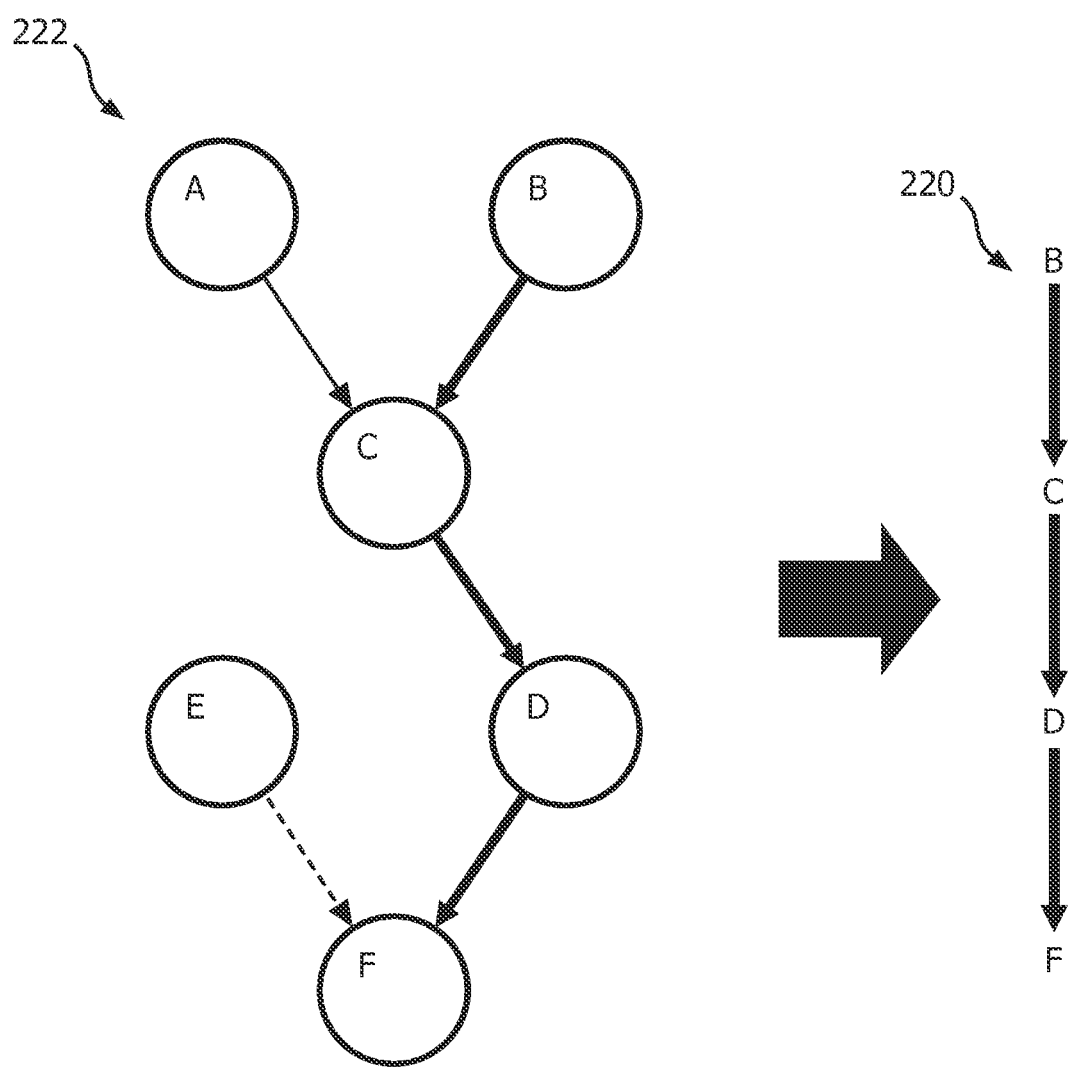
FIG. 8 illustrates visual representation that omits the node representation and emphasizes the information flow throughout the pathway.

FIG. 8 illustrates visual representation 220 that omits the node representation and emphasizes the information flow (the arrows) throughout the pathway 222. The information flow can now be considered as a series of modular units in all subsequent analysis. In one embodiment, a graph rewriting method is employed, which consists of a set of a graph rewrite rules in the form L→R where the L represents the pattern side and R is the replacement graph. In large pathways this is useful in order to see the true connections among key regulatory genes. As in the case of a visual grammar, for each application, different L→R rules are applied. As in the example shown in FIG. 8, the originating nodes of all the weak connections (or disrupted connections) are deleted thereby keeping the strongest information flow among the genes in the pathway.

Once the information flow is visualized, a visualization tool (FIG. 1) linked to the actionable information from the standpoint of the clinical oncologist is employed to facilitate clinical decision support. The clinical decision support system (FIG. 1) links the visualization of the pathway activity to a set of therapies that facilitate disrupting the activity of the pathway, acting on the key readout genes directly, etc. In some cases, the mechanism of action may not have been confirmed with detailed biological experiments. In that case, an association between information flow and therapy options can be made with a predefined set of labels describing the functional aspects of pathway activity. In this manner, the described systems and methods facilitate providing oncology decision support such as prognosis and therapy-response. Visual identification of and presentation of pathways with altered activity levels can be used for developing more individualized regimens for the cancer patients.

FIG. 9 illustrates a pathway visual grammar 230 example, which is a context free grammar defined by a (i) starting symbol (pathwayChart), (ii) terminal vocabulary (square, triangle, pentagon, arrow, denim texture, red color), (iii) non-terminal vocabulary (connectedNodes, node, nestedGeneShape, geometricObject, shape, color, texture, connector, molecularFuncShape) and (iv) set of productions (or rules). For instance, the pathway grammar includes starting with a pathway chart, and identifying a number of connected nodes in the pathway. The connected nodes are then concatenated in a node-connector-node format. Each node is then represented as a nested gene shape, which is further represented as either a geometric object or a molecular function shape. The geometric object is represented as a square shape in this example, with one or more of color and texture superimposed thereon. Connectors between nodes are also visually represented (e.g., as arrows or the like). Molecular function shapes such as transcription factors or non-coding RNA is represented by a pentagon and a triangle, respectively, in the example of FIG. 9.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

The invention claimed is:

1. A system that facilitates visualizing gene activity pathways, using a visual grammar that defines visual elements associated with gene expression, gene activity level, and information flow, for clinical decision support, including:
    a validated pathway database configured to store a plurality of validated pathways, each of which describes at least one interaction between a plurality of genes using the visual grammar; and
    a processor configured to visually represent gene activity level for at least one gene of the plurality of genes across a plurality of populations, retrieve a gene activity pathway from the validated pathway database, wherein the retrieved gene activity pathway includes the at least one gene, visually represent gene activity levels for all genes in the retrieved gene activity pathway, visually represent information flow through interactions between all genes in the retrieved gene activity pathway, link the visual representation of the information flow to actionable information for a clinician, wherein the actionable information comprises a set of therapies that facilitate disrupting activity of the retrieved gene activity pathway, and output the visual representation of the information flow and the linked actionable information to the clinician, wherein the processor is further configured to visually represent the gene activity levels using visual color in hue-saturation-brightness (HSB) space, different gene activity levels are assigned different visual colors, and the visual representation is generated using a continuous function.

* * * * *